(12) United States Patent
Danilovski et al.

(10) Patent No.: US 7,572,773 B2
(45) Date of Patent: *Aug. 11, 2009

(54) SINGLE DOSE FAST DISSOLVING AZITHROMYCIN

(75) Inventors: Aleksandar Danilovski, Rijeka (HR); Knezevic Zdravka, Zagreb (HR)

(73) Assignee: Pliva Hrvatska D.O.O., Zagreb (HR)

( * ) Notice: Subject to any disclaimer, the term of this patent is extended or adjusted under 35 U.S.C. 154(b) by 196 days.

This patent is subject to a terminal disclaimer.

(21) Appl. No.: 10/898,147

(22) Filed: Jul. 22, 2004

(65) Prior Publication Data

US 2005/0026851 A1 Feb. 3, 2005

Related U.S. Application Data

(60) Provisional application No. 60/490,187, filed on Jul. 24, 2003.

(51) Int. Cl.
*A61K 31/70* (2006.01)
(52) U.S. Cl. .......................................... 514/29; 536/7.4
(58) Field of Classification Search .................... 514/29
See application file for complete search history.

(56) References Cited

U.S. PATENT DOCUMENTS

| 5,605,889 | A  | * | 2/1997 | Curatolo et al. | ............... 514/29 |
| 6,703,372 | B1 | * | 3/2004 | Centellas et al. | .............. 514/29 |
| 6,861,413 | B2 |   | 3/2005 | Li et al. |  |
| 6,987,093 | B2 | * | 1/2006 | Dunne | ....................... 514/29 |
| 7,309,782 | B2 |   | 12/2007 | Li et al. |  |

FOREIGN PATENT DOCUMENTS

| EP | 0677530 | 10/1995 |
| EP | 0984020 | 3/2000 |
| EP | 1 400 528 | 3/2004 |
| WO | WO-02/085898 | 10/2002 |
| WO | WO-02/094843 | 11/2002 |
| WO | WO-03/077830 | 9/2003 |
| WO | WO-03/082889 | 10/2003 |

* cited by examiner

*Primary Examiner*—Elli Peselev
(74) *Attorney, Agent, or Firm*—Sterne Kessler Goldstein & Fox, PLLC (57) ABSTRACT

The present disclosure related to a method of treating an infection by oral administration of a single dose of a fast dissolving form of azithromycin. The disclosure also relates to a method of reducing the adverse effects arising from treatment of a subject having an infection by administering a single dose of a fast dissolving form of azithromycin.

11 Claims, 9 Drawing Sheets

SINGLE DOSE FAST DISSOLVING AZITHROMYCIN

Under 35 U.S.C. § 119(e), this application claims the benefit of prior U.S. Provisional Application No. 60/490,187, filed Jul. 24, 2003, the entire contents of which are incorporated herein by reference.

FIELD OF THE INVENTION

This invention relates to a method of treating an infection in mammals, including humans, by oral administration of a single dose of a fast dissolving form of azithromycin.

BACKGROUND OF THE INVENTION

9-Deoxo-9a-aza-9a-methyl-9a-homoerythromycin A (azithromycin) is the first and still the only marketed 15-member semi-synthetic macrolide antibiotic from the group of azalides [The Merck Index, 12$^{th}$ Ed. (1996), p. 157 (946)].

Azithromycin is an azalide antibiotic characterized by high intracellular and tissue concentrations and a very long half life. It has a broad spectrum of antimicrobial activity that includes common respiratory pathogens causing typical and atypical community acquired pneumonia (CAP), acute exacerbations of chronic bronchitis (AECB), laryngitis, phayringitis, sinusitis, acute otitis media (AOM) and other respiratory infections.

The synthesis of azithromycin is described in Belgian patent No. 892357 (see also U.S. Pat. No. 4,517,359). It has a well-known antibacterial spectrum (*J. Antimicrob. Chemother.*, 1987, 19, 275), mode of action (*Antimicrob. Ag. Chemother.*, 1987, 31, 1939) and pharmacology (*J. Antimicrob. Chemother.* 1993, 31, Suppl. E, 1-198).

Non-hygroscopic 9-deoxo-9a-aza-9a-methyl-9a-homoerythromycin A dihydrate was prepared as early as the mid-1980's by neutralization of an acidic solution of 9-deoxo-9a-aza-9a-methyl-9a-homoerythromycin A in an acetone-water mixture. Its crystal structure (single crystal) was evaluated upon recrystallization from ether, and was characterized by the orthorhombic space group P $2_1 2_1 2_1$. The unit cell parameters, namely crystal axes a=17.860 Å, b=16.889 Å and c=14.752 Å, and the angles between the crystal axes, $\alpha=\beta=\gamma=90°$, were published in 1987 at the Meeting of Chemists of Croatia (Book of Abstracts, Meeting of Chemists of Croatia, Feb. 19-20, 1987, p. 29). Thereafter, its crystal structure and preparation were described in detail (J. Chem. Res. (S), 1988, 152, Ibid., miniprint 1988, 1239; received Jun. 4, 1987; Cambridge Crystallographic Data Base: GEGJAD).

Azithromycin dihydrate is customarily orally administered as a solid dosage form or oral suspension at a dose of 250 mg once daily for five consecutive days, or at a dose of 500 mg once daily for three consecutive days, or at a dose of 500 mg as a single dose on the first day followed by 250 mg once daily on days 2 through 5.

It has been known that over the years many difficulties have arisen regarding patient compliance issues with a multi-day dosing regimen, because of forgetfulness as well as many other reasons. Pediatric patients in particular have difficulty in adhering to a multi day dosing scheme. For these reasons, it has been recognized that it would be desirable to administer an effective amount for treating respiratory infections in humans and other mammals with a single dose of azithromycin (see International Publication No. WO 03/018031). The population in third world countries, where respiratory infections are widespread, could benefit substantially from such single dosing regimen.

One difficulty or drawback observed during administration of a single dose of azithromycin dihydrate is that it involves gastrointestinal adverse events, sometimes referred to as side effects, that are incident to administration of oral azithromycin dihydrate dosages in excess of one gram. Reported adverse events include nausea, vomiting, abdominal pain and the like.

Extended release dosage compositions have been used in order to reduce the incidence and/or intensity of undesired effects following administration of a drug, by elimination of the peaks in drug concentration that often occur after administration of immediate release dosage forms (See Goodman and Gilman's The Pharmacological Basis of Therapeutics, 7$^{th}$ Edition, 1985, Chapter 1). Curatolo et al., in U.S. Pat. No. 6,068,859, describes the use of a controlled release dosage form of at least 1.0 gram to as high as 7.0 grams azithromycin in a single dose to treat respiratory infections. The dosage forms described in U.S. Pat. No. 6,068,859 are controlled release dosage forms, having specific delayed dissolution criteria (see FIG. 1 in U.S. Pat. No. 6,068,859).

It has now surprisingly been discovered that the adverse events that result from administration of, for example, single doses of a gram or more of azithromycin dihydrate can be overcome by orally administering to a patient in need of such treatment a single dose of an immediate release formulation containing a gram or more of a fast dissolving form of azithromycin, without the need for formulating an extended release dosage form.

DETAILED DESCRIPTION OF THE INVENTION

As used herein, with reference to the azithromycin dosage forms, the term "fast dissolving" denotes an azithromycin dosage form in which at least about 20% by weight of the azithromycin contained in the dosage form is dissolved within 5 minutes at pH 3.0 or higher. Preferably, at least about 20% by weight of the fast dissolving azithromycin dissolves within 5 minutes at pH 3.0, at least about 50% by weight dissolves within 10 minutes at pH 6.0 and at least about 60% by weight dissolves within 20 minutes at pH 6.8. The dosage forms described herein are effectively immediate release dosage forms.

As used herein, the term "single dose" denotes a dose that is administered only once over the whole anti-infective treatment period.

The term "about" generally means within 10%, preferably within 5%, and more preferably within 1% of a given value or range. Alternatively, the term "about" means within an acceptable standard error of the mean, when considered by one of ordinary skill in the art.

A "pharmaceutically acceptable" component, such as a pharmaceutically acceptable carrier or excipient, refers to a component that is useful in preparing a pharmaceutical composition that is generally safe, non-toxic and neither biologically nor otherwise undesirable, and includes a component that is acceptable for veterinary use as well as human pharmaceutical use.

Fast dissolving forms of azithromycin useful in the present invention are the substantially pure isostructural pseudopolymorphs of azithromycin of Formula (I) (disclosed in co-pending U.S. application Ser. No. 10/390,573, filed Mar. 17, 2003, the entire contents of which are hereby incorporated by reference).

(I)

wherein

S is an organic solvent which is at least partially miscible with water, x is 1, 1.25, 1.5 or 2, y is 0, 0.5, or 1, the pseudopolymorphs being characterized by the monoclinic space group $P\,2_1$ and a range of unit cell parameters of:

crystal axis lengths from a=15.5-17.0 Å, b=15.5-17.0 Å and c=17.5-19.5 Å, and angles between the crystal axes of $\alpha=\gamma=90°$ and $\beta=106\text{-}112°$ One fast dissolving azithromycin useful in the present invention is the polymorph of Formula Ia (hereinafter referred to as azithromycin monohydrate Ia). Fast dissolving azithromycin monohydrate Ia is a substantially pure isostructural pseudopolymorph of azithromycin wherein x=1 and y=0 and belongs to the monoclinic space group $P\,2_1$ having average unit cell parameters at 22° C. of:

a=16.368(5) Å,
b=16.301(3) Å,
c=18.408(5) Å,
$\alpha=\gamma=90°$, $\beta=110.04(2)$.

Another fast dissolving azithromycin useful in the present invention is the polymorph of Formula Ik. Polymorph Ik is a substantially pure isostructural pseudopolymorph of azithromycin wherein S represents glycerol, characterized by x=1.5 and y=0.5, and belongs to the monoclinic space group $P2_1$ having unit cell parameters at 22° C. of:

a=16.303(6) Å,
b=16.304(4) Å,
c=18.725(13) Å,
$\alpha=\gamma=90°$, $\beta=108.968(15)°$.

Oral Formulations of the Fast Dissolving Azithromycin

The formulations of the fast dissolving forms of azithromycin are administered orally, in the form of tablets, microparticles, mini tablets, capsules and oral solutions or suspensions, or powders for the preparation thereof.

In addition to the fast dissolving forms of azithromycin as the active substance for single dose administration, the pharmaceutical formulations may optionally include various standard pharmaceutical carriers and excipients, such as binders, fillers, buffers, lubricants, glidants, disintegrants, odorants, sweeteners, surfactants and coatings. Some excipients may have multiple roles in the formulations, e.g., act as both binders and disintegrants.

Examples of pharmaceutically acceptable disintegrants useful for oral formulations include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral formulations useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral formulations include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the formulations include, but are not limited to, magnesium stearate, talc, polyethylene glycol, polymers of ethylene oxide, sodium lauryl sulfate, magnesium lauryl sulfate, sodium oleate, sodium stearyl fumarate, DL-leucine and colloidal silicon dioxide Examples of suitable pharmaceutically acceptable odorants for the oral formulations include, but are not limited to, synthetic aromas and natural aromatic oils such as extracts of oils, flowers, fruits and combinations thereof. Preferable are vanilla and fruit aromas, including banana, apple, sour cherry, peach and similar aromas. Their use depends on many factors, the most important being the organoleptic acceptability for the population that will be taking the pharmaceutical formulations.

Examples of suitable pharmaceutically acceptable dyes for the oral formulations include, but are not limited to, synthetic and natural dyes such as titanium dioxide, beta-carotene and extracts of grapefruit peel.

Examples of useful pharmaceutically acceptable coatings for the oral formulations, typically used to facilitate swallowing, modify the release properties, improve the appearance, and/or mask the taste of the formulations include, but are not limited to, hydroxypropylmethylcellulose, hydroxypropylcellulose and acrylate-methacrylate copolymers.

Suitable examples of pharmaceutically acceptable sweeteners for the oral formulations include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Administration of a single dose solid oral dosage form containing more that one gram of the fast dissolving azithromycin monohydrate Ia has a significantly lower incidence of adverse events compared to administration of a comparable dose of the commercially available azithromycin dihydrate. Without wishing to be bound by theory, t is believed that reduced incidence of adverse events is due to the shorter contact of the fast dissolving azithromycin monohydrate Ia employed in the present invention with the gastrointestinal surface and its receptors, for example motilin receptors, for a shorter period of time than during administration of a comparable single dose of the commercially available azithromycin dihydrate.

In one embodiment, the single dose solid oral dosage form or oral suspension used in the present invention contains of more than about 1.0 gram of the fast dissolving form of azithromycin, for example the fast dissolving azithromycin monohydrate Ia, preferably an amount of about 1.0 to about 1.5 grams. In another embodiment, the dose is about 1.2 grams or more. In other embodiments, the single dose is selected from 1.1, 1.2, 1.3, 1.4, 1.5, 1.6, 1.7, 1.8, 1.9, and 2.0 grams.

The single dose of the solid oral dosage form or oral suspension containing a fast dissolving form of azithromycin, for example, the fast dissolving azithromycin monohydrate Ia, may be orally administered to humans, or other mammals, for the treatment of, but not limited to, community acquired pneumonia (CAP), acute exacerbations of chronic bronchitis (AECB), laryngitis, phayringitis, sinusitis, acute otitis media (AOM) and other respiratory infections.

In a preferred embodiment, a single dose of a solid oral dosage form or oral suspension containing between about 1.0 grams to about 1.5 grams of the fast dissolving azithromycin monohydrate Ia is administered orally to a patient afflicted with AECB.

The following examples illustrates the process of the present disclosure, but should not be construed as limiting the scope of this invention.

EXAMPLES

Example 1

Composition of the fast dissolving azithromycin monohydrate 1500 mg dispersible tablet or powder for oral suspension.

| FUNCTION | COMPOSITION | QUANTITY mg/tbl | % |
|---|---|---|---|
| Active substance | Azithromycin monohydrate equivalent to 1500 mg Azithromycin | 1528.29 | 36.56 |
| Binder | Ethyl cellulose aqueous dispersion | 162.18 | 3.72 |
| Alkaline salt | Tri-sodium phosphate anhydrous | 117.90 | 2.70 |
| Wetting agent | Sodium lauryl sulfate | 8.43 | 0.19 |
| Granulating agent | Glyceryl Behenate | 67.41 | 1.54 |
| Filler | Microcrystalline cellulose | 1086.21 | 24.88 |
| Filler | Starch (Corn Starch) | 724.14 | 16.59 |
| Filler | Lactose monohydrate | 30.00 | 0.69 |
| Sweetening agent | Aspartame | 90.00 | 2.06 |
| Gliding agent | Colloidal silica, anhydrous | 30.00 | 0.69 |
| Disintegrating agent | Amino-alkyl methacrylate copolymer E | 375.00 | 8.59 |
| Anti-adhering agent | Talc | 36.00 | 0.82 |
| Lubricating agent | Magnesium stearate | 42.00 | 0.96 |
| | Total: | 4365.00 | 100.00 |

Example 2

Dissolution Profiles of the Fast Dissolving Azithromycin Monohydrate vs. Commercial Azithromycin Dihydrate In order to compare the behavior in vitro of the fast dissolving azithromycin monohydrate (Formula Ia) with the commercial azithromycin dihydrate product, dissolution profiles have been determined at pH 1.2, pH 3.0, pH 6.0, and pH 6.8, at 37° C. The comparative dissolution profiles were determined in 900 ml buffer solution, at 100 rpm, by USP Method 2, PharmaTest Dissolution Tester, PTW SII; the content of dissolved azithromycin was measured by HPLC. The data thus obtained are plotted in FIGS. 1-4, respectively.

This azithromycin monohydrate of Formula Ia has a rapid dissolution profile, as shown in FIGS. 1-4, and dissolves faster that a comparable dose of the commercially available form of azithromycin dihydrate.

Example 3

Figure 1:
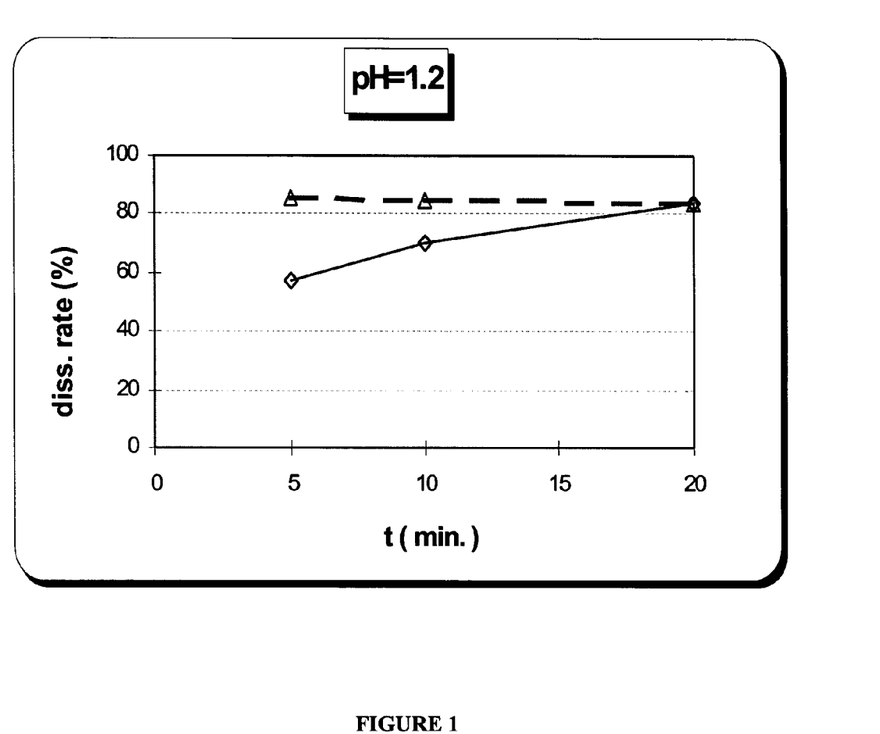
FIG. 1. Comparative dissolution profile of the fast dissolving azithromycin monohydrate Ia (triangles) and azithromycin dihydrate (diamonds) at pH=1.2 (USP app 2., 900 mL buffer, 100 rpm).
Figure 2:
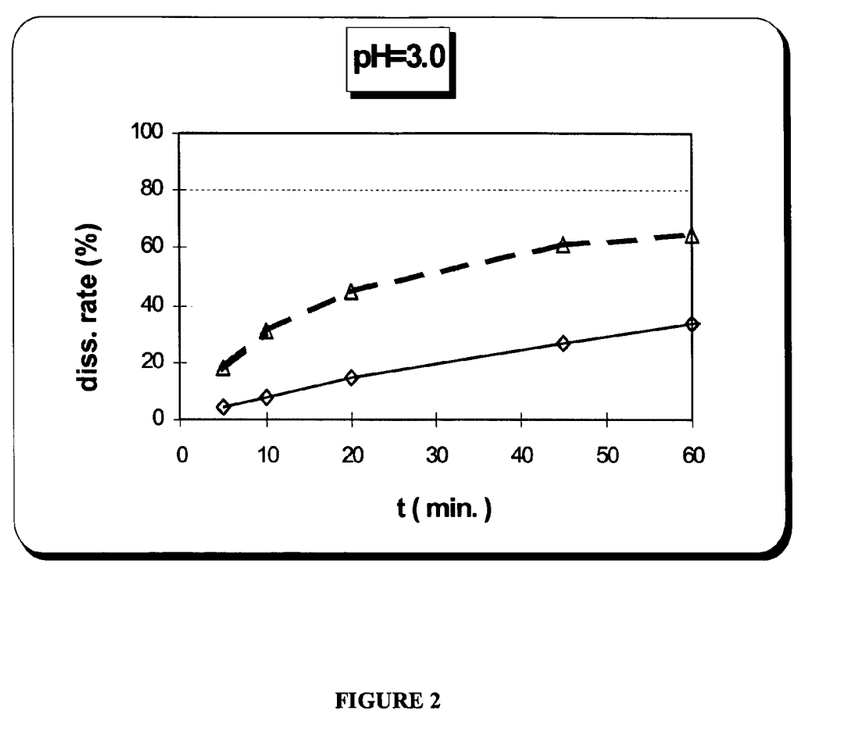
FIG. 2. Comparative dissolution profile of the fast dissolving azithromycin monohydrate Ia (triangles) and azithromycin dihydrate (diamonds) at pH=3.0 (USP app 2., 900 mL buffer, 100 rpm).
Figure 3:
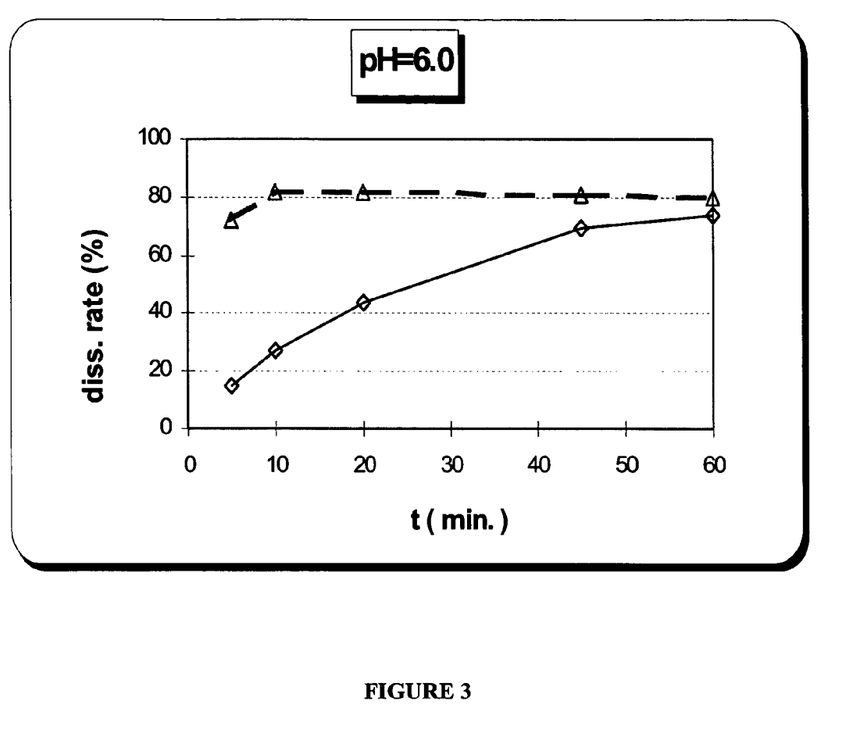
FIG. 3. Comparative dissolution profile of the fast dissolving azithromycin monohydrate Ia (triangles) and azithromycin dihydrate (diamonds) at pH=6.0 (USP app 2., 900 mL buffer, 100 rpm).
Figure 4:
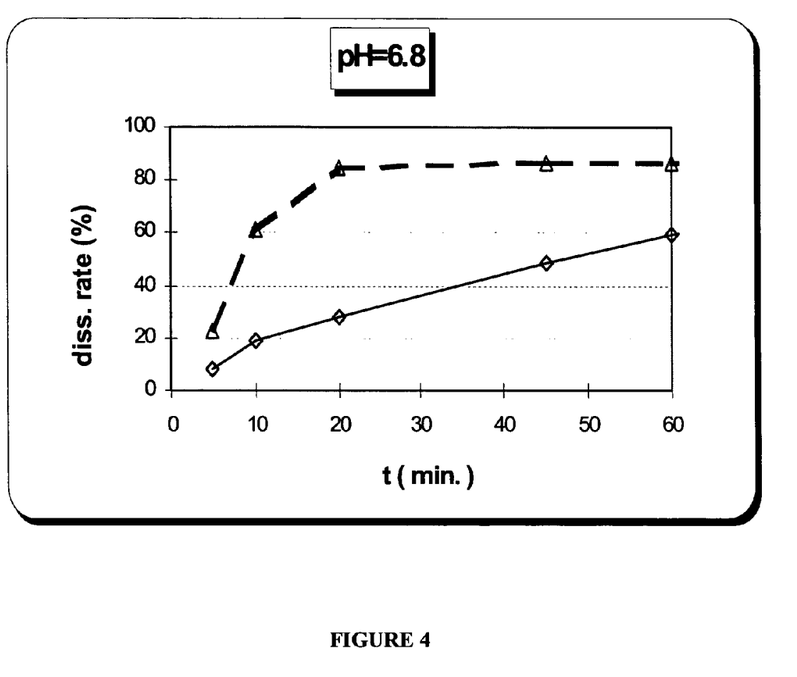
FIG. 4. Comparative dissolution profile of the fast dissolving azithromycin monohydrate Ia (triangles) and azithromycin dihydrate (diamonds) at pH=6.8 (USP app 2., 900 mL buffer, 100 rpm).
Figure 5:
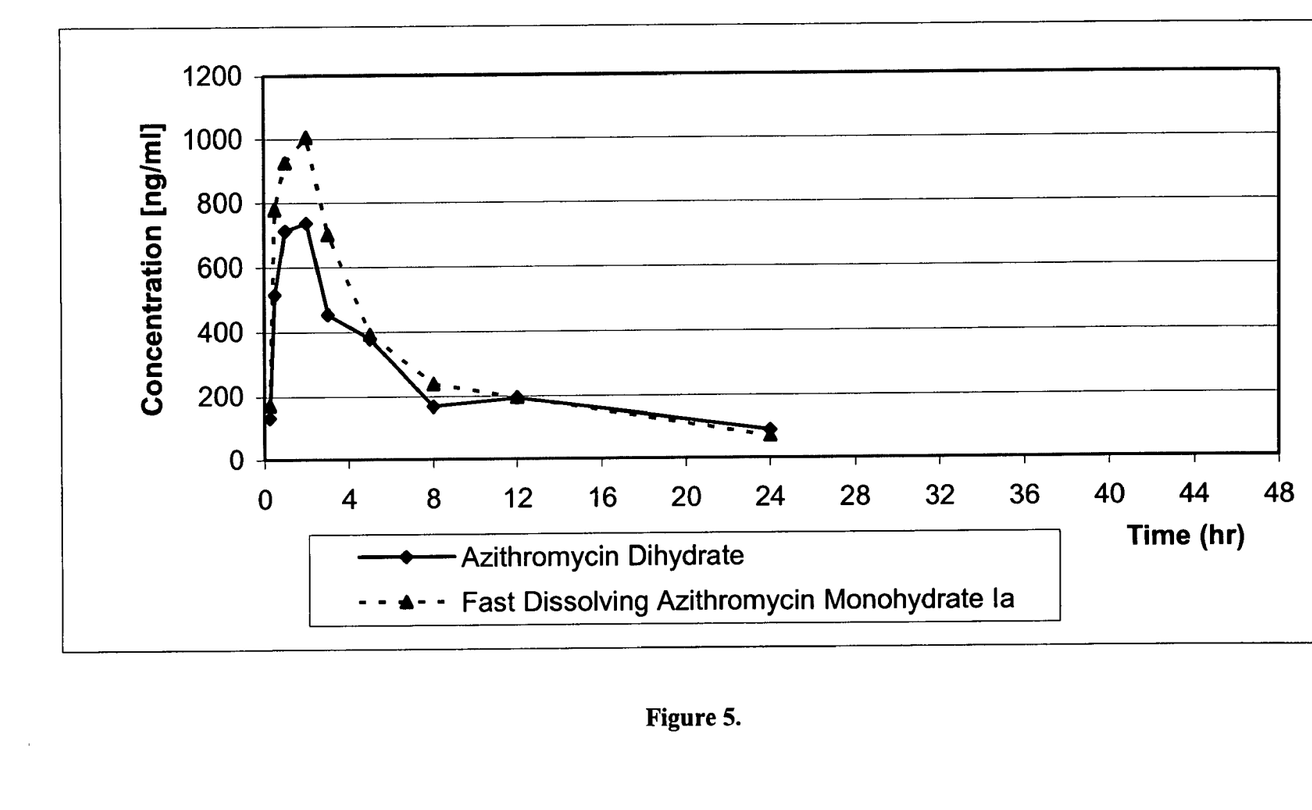
FIG. 5. Plasma profile of the fast dissolving azithromycin monohydrate Ia (triangles) and azithromycin dihydrate (diamonds) in rats after per os administration (50 mg/kg, aqueous suspension)
Figure 6:
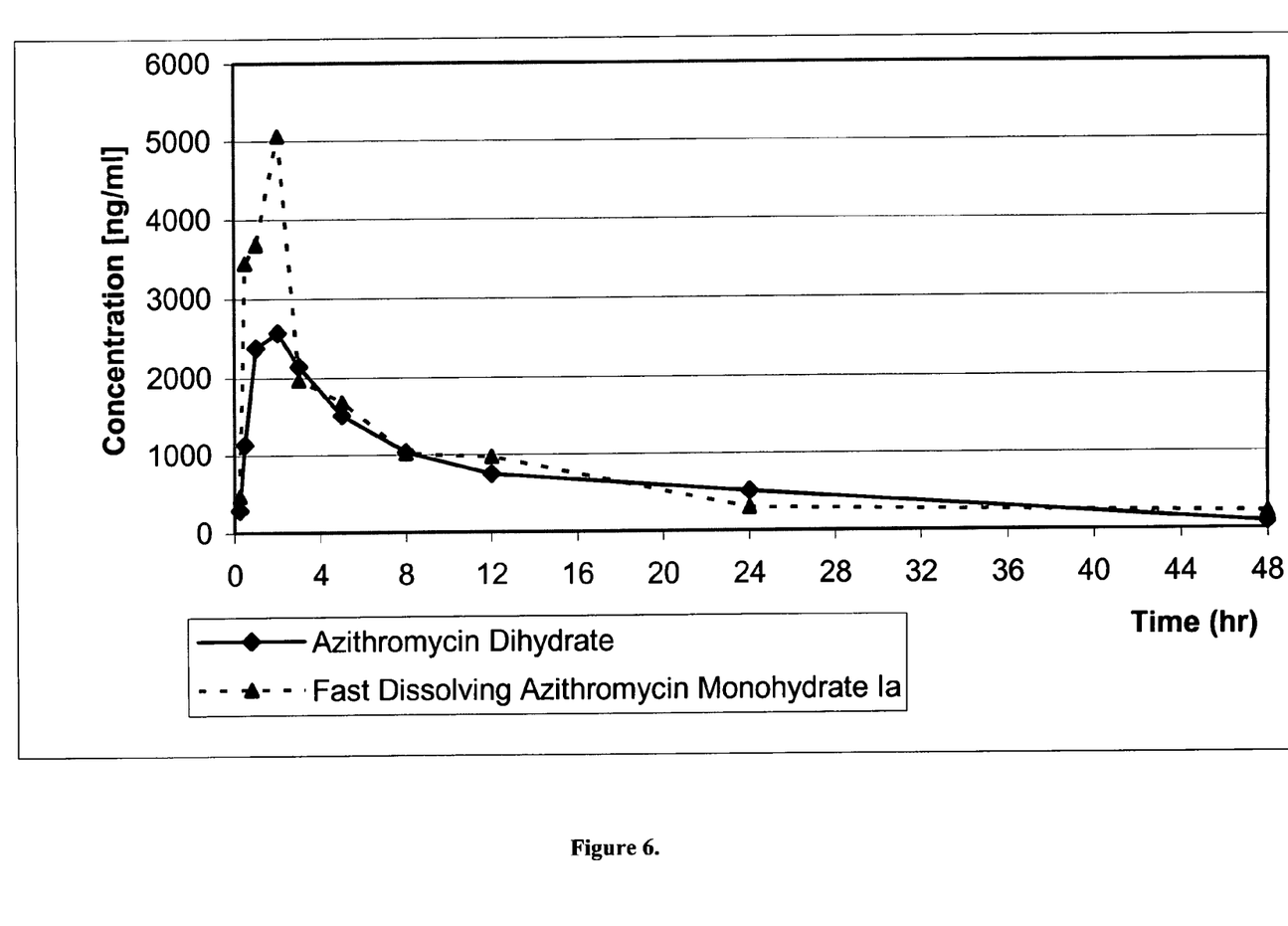
FIG. 6. Whole blood profile of the fast dissolving azithromycin monohydrate Ia (triangles) and azithromycin dihydrate (diamonds) in rats after per os administration (50 mg/kg, aqueous suspension)

In Vivo Pharmacokinetic Profiles Of Fast Dissolving Azithromycin Monohydrate Ia vs. Commercial Azithromycin Dihydrate (a) Rat Study In order to compare the behavior in vivo of the fast dissolving azithromycin monohydrate Ia with commercial azithromycin dihydrate product, plasma and whole blood concentration time curves have been determined in rats after p.o.

administration at a concentration of 50 mg/kg body weight. 32 animals (Wistar Han rats, fasted) were studied using a cross-over experimental design experiment. A non-compartmental analysis was used to determine the concentrations of the respective materials in whole blood and plasma as a function of time. The data thus obtained are set forth in FIGS. 5 and 6.

The pharmacokinetic parameters for the fast dissolving azithromycin monohydrate Ia and the commercial azithromycin dihydrate product in whole blood and in plasma in rats following a per os dose of 50 mg/kg body weight are set forth in Table 1 below.

TABLE 1

IN VIVO RAT PHARMACOKINETIC PARAMETERS FOR FAST DISSOLVING AZITHROMYCIN MONOHYDRATE IA AND COMMERCIAL AZITHROMYCIN DIHYDRATE

| 50 mg/kg suspension, p.o. | | Fast Dissolving Azithromycin Monohydrate (Ia) | Azithromycin Dihydrate | $\Delta_{Ia/dihydrate}$ (%) |
|---|---|---|---|---|
| Plasma | $C_{max}$ (ng/ml) | 1006 | 735 | +37 |
| | $AUC_{(0-12)}$ (nghr/ml) | 5148 | 3998 | +29 |
| Whole Blood | $C_{max}$ (ng/ml) | 5061 | 2569 | +97 |
| | $AUC_{(0-12)}$ (nghr/ml) | 21204 | 16721 | +27 |

As indicated in Table 1, higher concentrations of the fast dissolving azithromycin monohydrate Ia as compared with the commercial azithromycin dihydrate product are observed in both whole blood and plasma following per os administration in rats.

Higher AUC values were observed for the fast dissolving azithromycin monohydrate Ia during the first 12 hours following administration. The calculated AUC value for the first 0-12 hours, $AUC_{(0-12)}$, is surprisingly approximately 27% and 29% higher for the fast dissolving azithromycin monohydrate Ia, relative to the commercial azithromycin dihydrate product in both whole blood and plasma, respectively.

These results suggest faster absorption, higher bioavailability and more rapid distribution of the fast dissolving azithromycin monohydrate Ia into cells and/or tissues relative to the commercial azithromycin A dihydrate product.

(b) Human Study

In order to compare the behavior in vivo of the fast dissolving azithromycin monohydrate Ia with commercial azithromycin dihydrate product, plasma concentration time curves have been determined in humans after administration of a 500 mg aqueous azithromycin suspension. The test was an open, mono-centric, fasted human study. 6 human subjects were studied using a full cross-over experimental design experiment. In this experiment, 3 human subjects were administered an aqueous suspension of 500 mg of the fast dissolving azithromycin monohydrate (Ia), and the other 3 human subjects were administered an aqueous suspension of 500 mg of azithromycin dihydrate. After a washout period of at least one week, the 3 human subjects originally administered the fast dissolving azithromycin monohydrate (Ia), were administered an aqueous suspension of 500 mg of the azithromycin dihydrate, while the 3 human subjects originally administered the azithromycin dihydrate, were administered an aqueous suspension of 500 mg of the fast dissolving azithromycin monohydrate (Ia). This crossover experiment was repeated a total of three times by intubations of the test subjects: the first involved GI site-specific administration to the stomach, the second involved GI site-specific administration to the duodenum, and the third involved GI site-specific administration to the jejunum.

Figure 7:
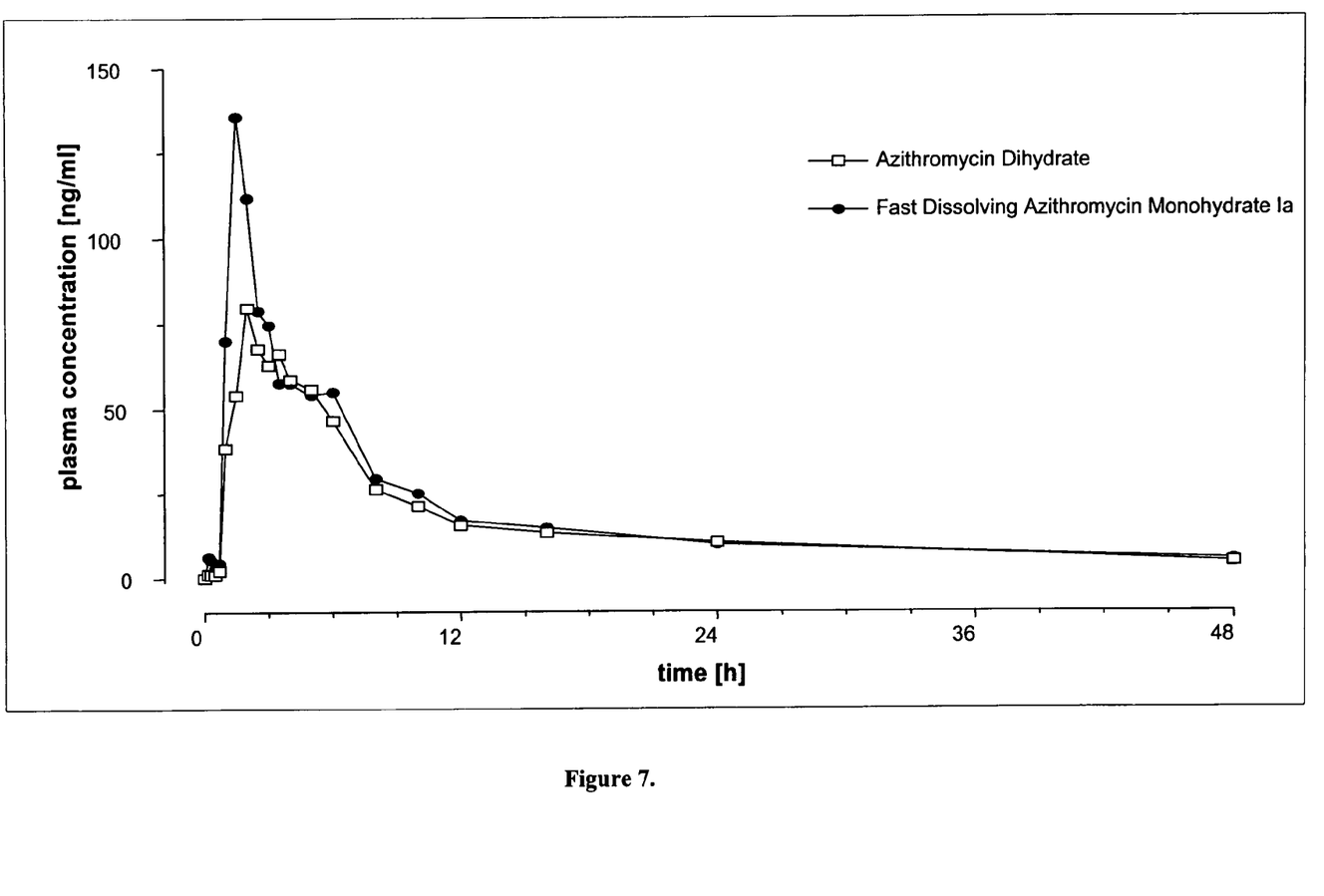
FIG. 7. Plasma profile of the fast dissolving azithromycin monohydrate Ia (circles) and azithromycin dihydrate (squares) in human after site specific administration to the stomach (500 mg, aqueous suspension)
Figure 8:
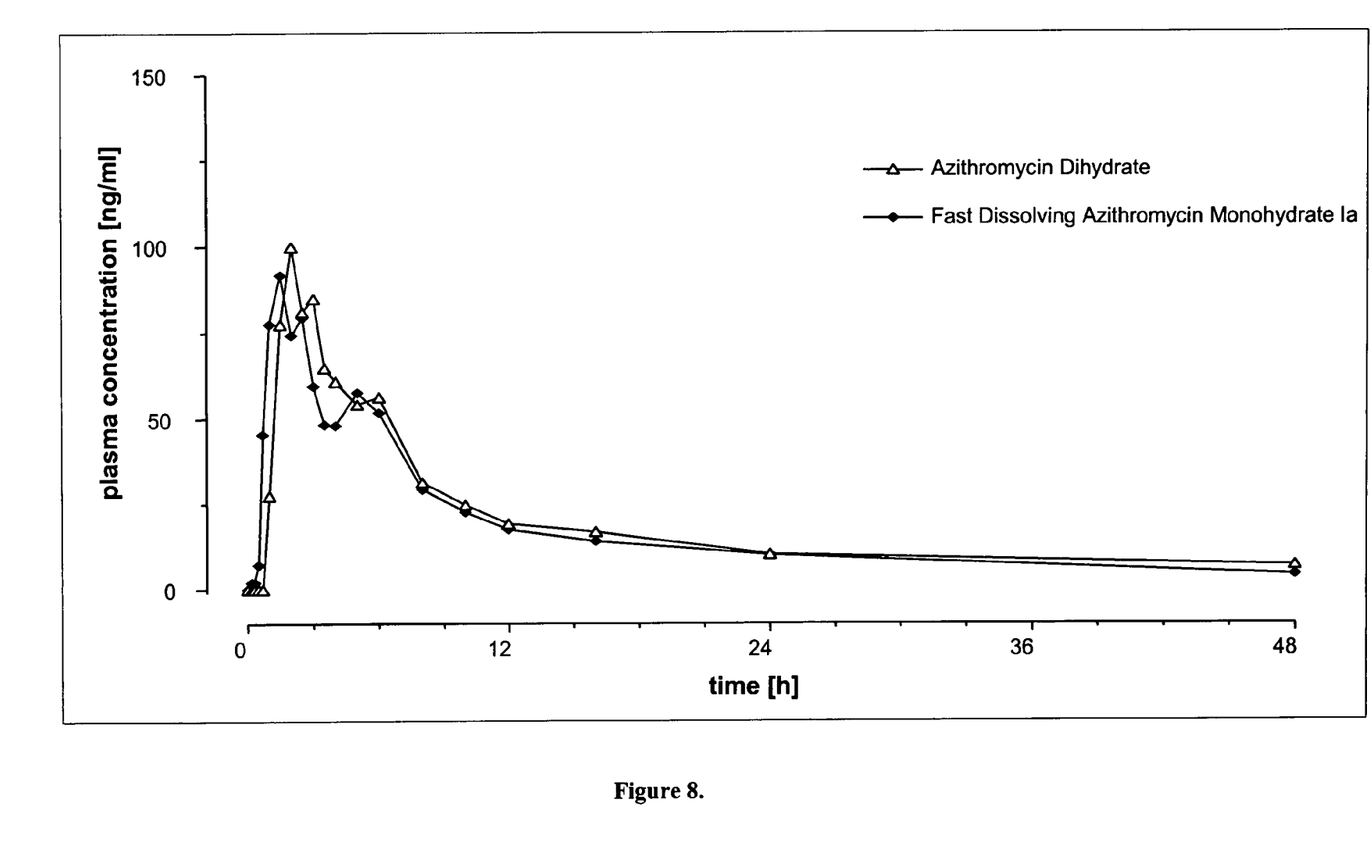
FIG. 8. Plasma profile of the fast dissolving azithromycin monohydrate Ia (diamonds) and azithromycin dihydrate (triangles) in human after site specific administration to the duodenum (500 mg, aqueous suspension)
Figure 9:
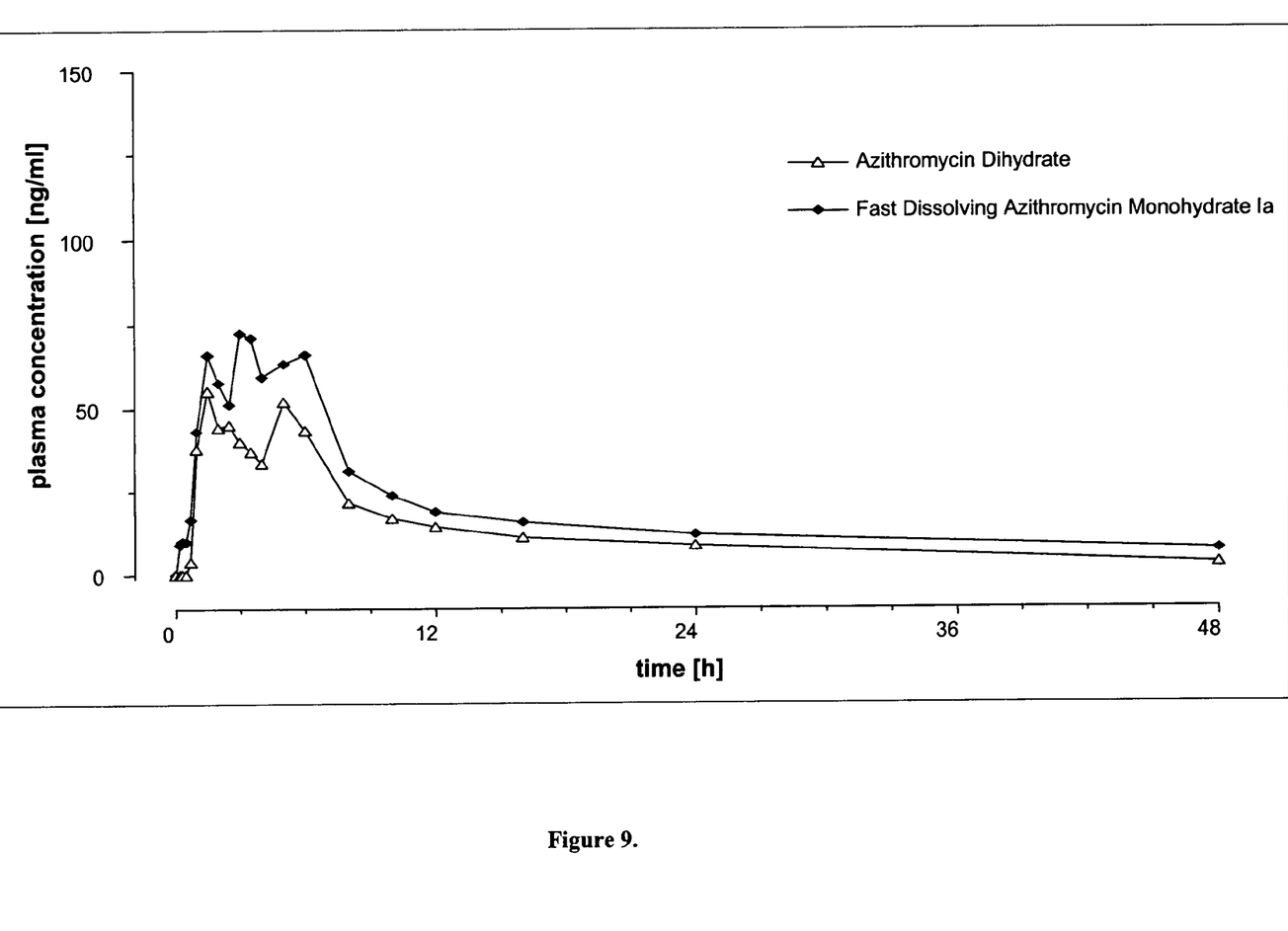
FIG. 9. Plasma profile of the fast dissolving azithromycin monohydrate Ia (diamonds) and azithromycin dihydrate (triangles) in human after site specific administration to the jejunum (500 mg, aqueous suspension)

The kinetics parameters were determined model-independently and the parameters were determined directly from the measured concentrations. The data thus obtained are set forth in FIGS. 7-9.

The pharmacokinetic parameters for the fast dissolving azithromycin monohydrate Ia and the commercial azithromycin dihydrate product in plasma in humans following administration of an aqueous suspension of 500 mg azithromycin are set forth in Table 2 below.

TABLE 2

IN VIVO RAT PHARMACOKINETIC PARAMETERS FOR FAST DISSOLVING AZITHROMYCIN MONOHYDRATE IA AND COMMERCIAL AZITHROMYCIN DIHYDRATE

| aqueous | 500 mg suspension | Fast Dissolving Azithromycin Monohydrate (Ia) | Azithromycin Dihydrate | $\Delta_{Ia/dihydrate}$ (%) |
|---|---|---|---|---|
| Stomach | $C_{max}$ (ng/ml) | 143 | 94 | +52 |
| | AUC (nghr/ml) | 813 | 683 | +19 |
| Duodenum | $C_{max}$ (ng/ml) | 129 | 117 | +10 |
| | AUC (nghr/ml) | 719 | 829 | −13 |
| Jejunum | $C_{max}$ (ng/ml) | 99 | 62 | +60 |
| | AUC (nghr/ml) | 836 | 422 | +98 |

As can be seen from Table 2, higher concentrations ($C_{max}$) and AUC values are observed after GI site-specific administration to the stomach and the jejunum of an aqueous suspension of 500 mg of the fast dissolving azithromycin monohydrate Ia when compared to similar administration of an aqueous suspension of 500 mg of the azithromycin dihydrate product.

The higher $C_{max}$ values observed after site specific administration to the stomach suggest that the azithromycin monohydrate Ia is dissolved faster, and hence enters the blood stream more quickly than the azithromycin dihydrate product. This is believed to result in a shorter contact time with the gastrointestinal surface and its receptors, for example, motilin receptors, for the fast dissolving monohydrate Ia when compared to the azithromycin dihydrate product, thereby resulting in a reduced incidence of adverse events observed during single dose administration of the fast dissolving azithromycin monohydrate Ia.

Experiment 4

Analysis of Adverse Events Observed During Human PK Study

A study of the adverse effects, such as stomach ache, vomiting, and nausea, observed during the human PK study described in Experiment 3b, revealed a total of 15 adverse events observed during the total of 36 single dose administrations conducted in the study (36 administrations results from 6 patients, administered separately azithromycin monohydrate Ia and azithromycin dihydrate product in (i) the stomach, (ii) the duodenum, and (iii) the jejunum).

Of the 15 adverse events, 10 events (67% of the total) were considered to be mild, of which 5 of these 10 mild events were observed during administration of the azithromycin dihydrate product; 4 events (27% of the total) were considered to be moderate, of which 3 of these 4 moderate events were observed during administration of the azithromycin dihydrate product; and 1 event (6% of the total) was considered to be severe. This single severe event was observed during administration of the azithromycin dihydrate product.

Of the 15 total adverse events observed during the human PK study, 12 events (80% of the total) were determined to have no causal relationship (i.e., these 12 events were related to the way of administration); 3 events (1 severe and 2 mild, 20% of the total) were determined to have a possible causal relationship (of which, all three events were related to administration of the azithromycin dihydrate product); and no events were determined to have a probable causal relationship.

These results indicate that single dose administration of the fast dissolving azithromycin monohydrate Ia has a lower incidence of adverse effects when compared to single dose administration of a comparable amount of azithromycin dihydrate product.

Example 5

Dissolution Profiles of the Fast Dissolving Azithromycin Polymorph Ik vs. Commercial Azithromycin Dihydrate In order to compare the behavior in vitro of the fast dissolving azithromycin polymorph (Formula Ik) with the commercial azithromycin dihydrate product, dissolution profiles have been determined at pH 6.0 at 37° C. The comparative dissolution profiles were determined by USP Method 2, PharmaTest Dissolution Tester, PTW SII; the content of dissolved azithromycin was measured by HPLC. The data thus obtained are set forth in Table 3.

The azithromycin polymorph of Formula Ik has a rapid dissolution profile and dissolves faster that a comparable dose of the commercially available form of azithromycin dihydrate.

TABLE 3

PERCENT AZITHROMYCIN PSEUDOPOLYMORPH Ik AND COMMERCIAL AZITHROMYCIN DIHYDRATE PRODUCT DISSOLVED

| Time | Commercial 9-deoxo-9a-aza-9a-methyl-9a-homoerythromycin A Dihydrate | 9-deoxo-9a-aza-9a-methyl-9a-homoerythromycin A Pseudopolymorph Ik (Example 6) |
|---|---|---|
| Minutes | pH 6 (37° C.) | pH 6 (37° C.) |
| 5 | 14.5 | 99.8 |
| 10 | 27.3 | 99.9 |
| 20 | 44.2 | 97.1 |
| 45 | 69.1 | 97.6 |

The present invention is not limited in scope by the specific embodiments described herein. Various modifications of the invention in addition to those described herein will become apparent to those skilled in the art from the foregoing description. Such modifications are intended to fall within the scope of the appended claims. All patents, applications, publications, test methods, literature, and other materials cited herein are hereby incorporated by reference.

What is claimed is:

1. A method of treating a respiratory infection in a mammal comprising providing a solid single dose of a fast dissolving form of azithromycin, wherein the fast dissolving form of azithromycin is a substantially pure isostructural pseudopolymorph of azithromycin monohydrate, with average unit cell parameters at 22° C. of:
a=16.368(5) Å,
b=16.301(3) Å,
c=18.408(5) Å,
α=γ=90°, and
β=110.04(2)°,
and administering the dose to a mammal in need of such treatment.

2. The method of claim 1, wherein the dose is greater than about 1.0 grams.

3. The method of claim 1, wherein the dose is between about 1.0 grams and about 1.5 grams.

4. The method of claim 1, wherein the dose is 1.5 grams.

5. A method of reducing the incidence of adverse side events arising from treating a respiratory infection in a mammal comprising providing a solid single dose of a fast dissolving form of azithromycin, wherein the fast dissolving form of azithromycin is a substantially pure isostructural pseudopolymorph of azithromycin monohydrate, with average unit cell parameters at 22° C. of
a=16.368(5) Å,
b=16.301(3) Å,
c=18.408(5) Å,
α=γ=90°, and
β=110.04(2)°,
and administering the dose to a mammal in need of such treatment.

6. The method of claim 5, wherein the dose is greater than about 1.0 grams.

7. The method of claim 5, wherein the dose is between about 1.0 grams and about 1.5 grams.

8. The method of claim 5, wherein the dose is 1.5 grams.

9. A method of treating a respiratory infection in a mammal comprising providing a solid single dose of an oral dosage form comprising at least one gram of a fast dissolving form of azithromycin, wherein at least about 20% by weight of the azithromycin contained in the dosage form dissolves within 5 minutes at pH 3.0 or higher, wherein the fast dissolving form of azithromycin is a substantially pure isostructural pseudopolymorph of azithromycin monohydrate, with average unit cell parameters at 22° C. of:
a=16.368(5) Å,
b=16.301(3) Å,
c=18.408(5) Å,
α=γ=90°, and
β=110.04(2)°,
and administering the dose to a mammal in need of such treatment.

10. The method of claim 1, wherein the respiratory infection is selected from community acquired pneumonia, acute exacerbations of chronic bronchitis, laryngitis, and phayringitis.

11. The method of claim 1, wherein the solid dose is in the form of a tablet, micro particle, capsule, or powder.

* * * * *